US00PP16155P3

(12) United States Plant Patent
Leue

(10) Patent No.: US PP16,155 P3
(45) Date of Patent: Dec. 13, 2005

(54) ***HIBISCUS* PLANT 'BAHLIBRED'**

(50) Latin Name: *Hibiscus moscheutos*
Varietal Denomination: Balhibred

(75) Inventor: Ellen Leue, DeKalb, IL (US)

(73) Assignee: PanAmerican Seed, a division of Ball Horticultural Company, West Chicago, IL (US)

( * ) Notice: Subject to any disclaimer, the term of this patent is extended or adjusted under 35 U.S.C. 154(b) by 279 days.

(21) Appl. No.: 10/627,223

(22) Filed: Jul. 25, 2003

(65) Prior Publication Data

US 2005/0022278 P1 Jan. 27, 2005

(51) Int. Cl.[7] ..... A01H 5/00

(52) U.S. Cl. ..... Plt./257

(58) Field of Search ..... Plt./257

*Primary Examiner*—Kent Bell
(74) *Attorney, Agent, or Firm*—Wood, Phillips, Katz, Clark & Mortimer

(57) ABSTRACT

A new and distinct cultivar of *Hibiscus moscheutos* plant named 'Balhibred', characterized by its upright and uniform plant habit, large, deep burgundy red-colored flowers, and light green-colored leaves.

1 Drawing Sheet

Latin name of the genus and species of the plant claimed: *Hibiscus moscheutos.*
Variety denomination: 'Balhibred'.

BACKGROUND OF THE INVENTION

The present invention relates to a new and distinct cultivar of *Hibiscus,* botanically known as *Hibiscus moscheutos,* hereinafter referred to by the name 'Balhibred'.

The new *Hibiscus* is a product of a planned breeding program conducted by the inventor in Elburn, Ill. The objective of the breeding program was to create new well-branched *Hibiscus* cultivars with desirable flower color, and uniform and compact plant habit appropriate for container production.

The new *Hibiscus* originated from a cross made by the inventor in Elburn, Ill. in 2000, of the *Hibiscus moscheutos* proprietary breeding line 114-7-2 (not patented), as the female, or seed, parent with the *Hibiscus moscheutos* proprietary breeding line 116-23-5 (not patented), as the male, or pollen, parent. The female parent, *Hibiscus moscheutos* proprietary breeding line 114-7-2, is fairly tall with a good habit and deep red flowers. The male parent, *Hibiscus moscheutos* proprietary breeding line 116-23-5 has medium height with a good habit and medium pink flowers and good fertility.

Compared to plants of the female parent, *Hibiscus moscheutos* proprietary breeding line 114-7-2, the cultivar 'Balhibred' is more compact, better branched, and more free flowering than the female parent.

Compared to plants of male parent, *Hibiscus moscheutos* proprietary breeding line 116-23-5, the flowers of the cultivar 'Balhibred' are deep burgundy red whereas the flowers of the male parent are medium pink. The cultivar 'Balhibred' is more vigorous and more free flowering, and has larger flowers than the male parent.

The cultivar 'Balhibred' was discovered and selected by the inventor as a flowering plant within the progeny of the stated cross in a controlled environment in Elburn, Ill., on Aug. 7, 2001. The cultivar 'Balhibred' is perennial to Zone 5.

Both parents have a degree of homozygosity such that the progeny of the cross 114-7-2 times 116-23-5 are phenotypically uniform and essentially identical to 'Balhibred'. Removal of the terminal apex will improve branching in asexually reproduced plants. Accordingly, plants that are phenotypically identical to 'Balhibred' can be produced by sexual reproduction as well as asexual reproduction.

Asexual reproduction of the new *Hibiscus* by vegetative terminal cuttings taken in a controlled environment in Santa Paula, Calif. has shown that the unique features of this new *Hibiscus* are stable and reproduced true to type in successive generations.

SUMMARY OF THE INVENTION

The following traits have been repeatedly observed and are determined to be the unique characteristics of 'Balhibred'. These characteristics in combination distinguish 'Balhibred' as a new and distinct cultivar:

1. Compact, upright, and symmetrical plant habit that is suitable for container production;
2. Early to flower;
3. Bushy, well branched;
4. Large flowered and floriferous; and
5. Deep burgundy red flowers.

Plants of the new *Hibiscus* 'Bahlibred' can be compared to plants of the *Hibiscus* Disco Belle Series Pink (not patented). In side-by-side comparisons conducted in Santa Paula, Calif., plants of the new *Hibiscus* 'Balhibred' differ from plants of Disco Belle Series Pink in the following characteristics:

1. Plants of the new *Hibiscus* 'Balhibred' are 20% more compact;

2. Plants of the new *Hibiscus* 'Balhibred' are earlier to flower by approximately one week;
3. Plants of the new *Hibiscus* 'Balhibred' have more branches;
4. Plants of the new *Hibiscus* 'Balhibred' are branched more uniformly; and
5. Plants of the new *Hibiscus* 'Balhibred' are more floriferous.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph differ from the color values cited in the detailed botanical description that accurately describe the colors of the new *Hibiscus*.

The photograph comprises a side perspective view of a single flowering plant of 'Balhibred' grown in a container.

DETAILED BOTANICAL DESCRIPTION

The cultivar 'Balhibred' has not been observed under all possible environmental conditions. The phenotype may vary somewhat with variations in environment and cultural practices such as temperature, light intensity, water status and/or fertilizer rate or type without, however, any variance in genotype.

The photographs and following observations, measurements and values describe plants grown in Santa Paula, Calif. with 1 plant per 15 cm container in glass-covered greenhouses during the winter and spring under conditions which closely approximate commercial production. During the production of the plants, day temperatures ranged from 18 to 23° C. and night temperatures ranged from 16 and 21° C. Plants and controls were treated with plant growth regulators as follows: one time with CYCOCEL at 250 ppm, followed by two times with a mixture of B-9 at 2500 ppm and CYCOCEL at 500 ppm. Plants were approximately 6 months old when the description, photographs and color values were determined. The chart used in the identification of the colors described herein is The R.H.S. Colour Chart of The Royal Horticultural Society, London, England. The color values were determined on Jun. 23, 2003 between 10:00 am and 2:00 pm under natural daylight conditions.

Botanical classification: *Hibiscus moscheutos* cultivar 'Balhibred'.

Parentage:

*Female or seed parent.*—Proprietary selection of *Hibiscus moscheutos* identified as code number 114-7-2, not patented.

*Male or pollen parent.*—Proprietary selection of *Hibiscus moscheutos* identified as code number 116-23-5, not patented.

Propagation:

*Type.*—By vegetative terminal cuttings.

*Time to initiate roots.*—About 17 days at temperatures of 27–29° C. days and 21 to 22° C. nights.

*Time to develop roots.*—About 26 days at temperatures of 27–29° C. days and 21 to 22° C. nights.

*Root description.*—Thick, fibrous and white in color.

Plant description:

*Plant form and growth habit.*—Upright, lateral branches, vigorous growth habit.

*Branching habit.*—Freely branched, one to six lateral branches.

*Plant height.*—65 cm.

*Plant diameter* (*area of spread*).—55 cm.

*Lateral branch description.*—Length: 45 cm. Diameter: 7 mm at base to 3 mm at tip. Texture: Immature: Smooth. Texture: Mature: Woody and rough. Color: Immature: 138B. Color: Mature: 138B.

*Foliage description.*—Arrangement: Alternate. Length: 12 cm, from central stem. Width: 9.5 cm. Shape: Ovate. Apex: Acute to narrowly acuminate. Base: Cordate to obtuse. Margin: Entire to sinuate. Aspect: Concave. Texture: Upper surface: Glabrous. Texture: Lower surface: Glabrous. Venation pattern: Palmate. Color: Young foliage, upper surface: 137C. Young foliage, lower surface: 138C. Mature foliage, upper surface: 146A. Mature foliage, lower surface: 146B. Venation, upper surface: 137C. Venation, lower surface: 137C. Petiole: Length: 3.5 cm. Diameter: 2 mm. Texture: Upper surface: Puberulent. Texture: Lower surface: Puberulent. Color: 138B.

Flower description:

*Flower arrangement.*—5 or more apical buds, side facing.

*Flower appearance.*—5 rounded petals, red, open about 1 day.

*Natural flowering season.*—Spring and summer.

*Flower diameter.*—18.5 cm.

*Flower length* (*height*).—4 cm.

*Flower bud* (*just before showing color*).—Rate of opening: Approximately 2 days. Length: 2.5 cm. Diameter: 2 cm. Shape: Ovate. Color: 146A.

*Petals.*—Arrangement: 5 overlapping petals, fused at base. Length: 9 cm. Width: 11.5 cm. Shape: Broad spatulate. Apex: Rounded. Base: Attenuate. Margin: Entire. Texture: Upper surface: Glabrous and leathery. Texture: Lower surface: Glabrous. Color: When opening, upper surface: 60A. Venation: 59A. When opening, lower surface: 60A. Venation: 60B. Base: 59A (ring). Fully opened, upper surface: 60A. Venation: 59A. Fully opened, lower surface: 60A. Venation: 60B. Base: 59A (ring). Throat: 53B.

*Sepals.*—Appearance: 5 sepals fused into a star shaped calyx. Length: 3.2 cm. Width: 2.6 cm. Shape: Deltoid. Apex: Cuspidate. Margin: Entire. Texture: Inner (upper) surface: Glabrous. Texture: Outer (lower) surface: Glabrous. Color: Inner (upper) surface: 137C. Color: Outer (lower) surface: 138B.

*Bracts.*—Appearance: 9 bracts fused at base. Length: 16 mm. Width: 2 mm at base to 1 mm at tip. Shape: Acicular. Apex: Acuminate. Margin: Entire. Texture: Upper surface: Puberulent. Texture: Lower surface: Glabrous. Color: Upper surface: 144A. Color: Lower surface: 138A.

*Peduncles.*—Length: From 5.5 to 3.3 cm. Diameter: 2 mm. Angle: Upright, about 60 degrees. Strength: Strong. Texture: Puberulent. Color: 146C.

*Reproductive organs.*—Androecium: Stamen number: Numerous, approximately 100. Filament length: Approximately 5 mm. Color: Filament: 53D. Anther shape: Globular. Anther size: Approximately 1 mm by 1 mm. Color: Anther: 16D. Amount of pollen: Abundant. Color: Pollen: Approximately 15C. Gynoecium: Pistil length: 4.2 cm. Pistil diameter apex: 5 mm. Pistil diameter base: Approximately 1 cm. Style texture: Puberulent. Color: Style: 52A (apex), 52D (base). Stigma appearance: 5 rounded. Stigma diameter: Approximately 2 mm. Color: Stigma: 46A. Color: Ovary: 155B.

*Seed.*—The cultivar 'Balhibred' will set seed when exposed to pollinating insects in an outdoor situation. Size: Approximately 3 mm. Shape: Spherical. Texture: Smooth. Color: Darker than 200A.

Disease resistance: Resistance to common diseases of *Hibiscus* have not been observed.

What is claimed is:

1. A new and distinct cultivar of *Hibiscus moscheutos* plant named 'Balhibred', substantially as herein shown and described.

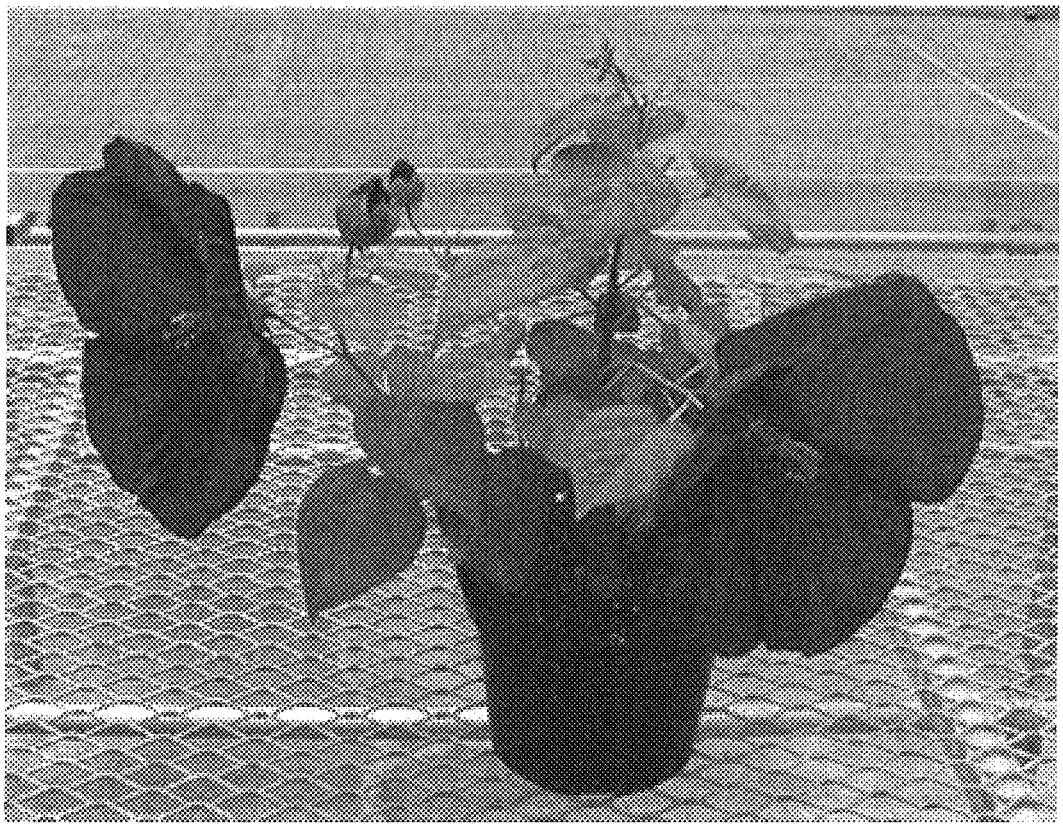

* * * * *